United States Patent
Kwon et al.

(10) Patent No.: US 7,595,080 B2
(45) Date of Patent: Sep. 29, 2009

(54) **METHOD FOR PREPARING AN EXTRACT OF FRUIT OF *SOPHORA JAPONICA* CONTAINING ISOFLAVONE**

(75) Inventors: Suk-Hyung Kwon, Seoul (KR); Bo-Sik Hwang, Gyeonggi-do (KR); Kuk-Hwan Kim, Chungcheongbuk-do (KR); Seung-Hwan Lee, Seoul (KR); Eun-Ju Yoon, Daejeon (KR); Seung-Hee Lee, Chungcheongbuk-do (KR)

(73) Assignee: Rexgenebiotech Co., Ltd., Chungcheongbuk-Do (KR)

( * ) Notice: Subject to any disclaimer, the term of this patent is extended or adjusted under 35 U.S.C. 154(b) by 673 days.

(21) Appl. No.: 10/577,553

(22) PCT Filed: Dec. 24, 2003

(86) PCT No.: PCT/KR03/02841

§ 371 (c)(1),
(2), (4) Date: Apr. 28, 2006

(87) PCT Pub. No.: WO2005/042757

PCT Pub. Date: May 12, 2005

(65) Prior Publication Data

US 2007/0031573 A1 Feb. 8, 2007

(30) Foreign Application Priority Data

Oct. 31, 2003 (KR) .................. 10-2003-0077000

(51) Int. Cl.
*A23L 1/20* (2006.01)
(52) U.S. Cl. .................. 426/655; 426/430; 426/634
(58) Field of Classification Search .................. 426/429, 426/430, 655; 435/41; 424/757
See application file for complete search history.

(56) References Cited

U.S. PATENT DOCUMENTS

| | | | |
|---|---|---|---|
| 5,851,792 A * | 12/1998 | Shen et al. .................. 435/68.1 |
| 2002/0015776 A1 | 2/2002 | Bryan et al. |
| 2002/0041907 A1* | 4/2002 | Liviero et al. ................ 424/725 |
| 2002/0142012 A1* | 10/2002 | Lanzendorfer et al. ....... 424/401 |
| 2003/0118675 A1 | 6/2003 | Waggle et al. |
| 2003/0180394 A1* | 9/2003 | Erdelmeier et al. ......... 424/725 |

FOREIGN PATENT DOCUMENTS

KR 10-2001-0081369 A 8/2001
WO 99/06057 2/1999

OTHER PUBLICATIONS

Joo et al., "Isoflavones Extracted from *Sophorae fructus* Upregulate IGF-1 and TGF-β and Inhibit Osteoclastogenesis in Rat Born Marrow Cells," *Arch. Pharm. Res.*, 2004, vol. 27, No. 1, pp. 99-105, Archives of Pharmacal Research, Seoul, Republic of Korea.
Joo et al., "Inhibition of IL-1β and IL-6 in Osteoblast-Like Cell by Isovlavones Extracted from *Sophorae fructus*," *Arch. Pharm. Res.*, 2003, vol. 26, No. 12, pp. 1029-1035, Archives of Pharmacal Research, Seoul, Republic of Korea.

* cited by examiner

*Primary Examiner*—Keith D Hendricks
*Assistant Examiner*—Jenna A Watts
(74) *Attorney, Agent, or Firm*—Buchanan Ingersoll & Rooney, PC

(57) ABSTRACT

The present invention relates to a method for preparing a *Sohporae Fructus* extract containing isoflavone. More particularly, the present invention relates to a method for preparing a *Sohporae Fructus* extract containing isoflavone in high concentration, which is characterized by the steps of hydrothermal extraction, enzyme treatment and ethanol extraction of *Sophorae Fructus*. A *Sophorae Fructus* extract containing a high concentration of aglycon-type isoflavone having an excellent bio-absorbability can be prepared by the method of the present invention.

8 Claims, 2 Drawing Sheets

METHOD FOR PREPARING AN EXTRACT OF FRUIT OF *SOPHORA JAPONICA* CONTAINING ISOFLAVONE

FIELD OF THE INVENTION

The present invention relates to a method for preparing a *Sohporae Fructus* extract. More particularly, the present invention relates to a method for preparing a *Sohporae Fructus* extract containing isoflavone in high concentration.

BACKGROUND OF THE INVENTION

Isoflavone is also called as phytoestrogen because it has a similar function to the female hormone, estrogen. Isoflavone has been reported to have various physiological activities such as prevention of osteoporosis, anticancer activity especially for breast cancer and prostate cancer, lowering cholesterol, antioxidation and the like (Toda T. et al., *Food and Development*, 31(6), 44~47, 1996; Murphy P. A., *Food Technol.*, 36, 60~64, 1982; Adlercreutz. C. H. et al., *J. Nutr.*, 125(3S), 757~770, 1995).

Genistein, daidzein and glycitein are typical isoflavones, which have been known to exist in leguminous plants, arrowroot and some other plants. So, a lot of studies on methods for preparing plant extracts containing isoflavone have conducted.

A method for preparing a plant extract containing isoflavone using soy beans as a raw material has been mainly studied. For example, Korean patent No. 388511 discloses a method for preparing a soy bean extract containing isoflavone, which is characterized by the steps of extracting soy beans using aliphatic alcohol or the mixture of aliphatic alcohol and water, concentrating the extract, treating the concentrate with aliphatic carbohydrate and extracting it again using aliphatic alcohol. Korean patent publication No. 2001-47621 discloses a method for preparing a soy bean extract containing isoflavone, which is characterized by the steps of adding hexane to crushed soy beans, removing lipid components by perfusive extraction, adding aqueous solution of methanol to the remnants for further perfusive extraction, filtering, concentrating under a reduced pressure and vacuum drying. Also, Korean patent No. 348148 discloses a *Puerariae Radix* extract containing isoflavone which is prepared by dipping *Puerariae Radix* in aqueous solution of alcohol, filtering, freezedying and hydrolyzing with acid or base.

Meanwhile, in order to prepare an extract containing isoflavone in higher concentration, it is required to secure a new isoflavone source or to develop an optimum method of extraction.

OBJECT OF THE INVENTION

The present inventors optimized a series of conditions for extracting isoflavone in high concentration using *Sophorae Fructus*, fruit of *Sophora japonica Linne* as a source of isoflavone, identified that a *Sophorae Fructus* extract containing a high concentration of isoflavone could be obtained by the same method and thus completed the present invention.

Accordingly, it is an object of the invention to provide a method for preparing a *Sophorae Fructus* extract containing a high concentration of isoflavone.

DETAILED DESCRIPTION OF THE INVENTION

Figure 1A:
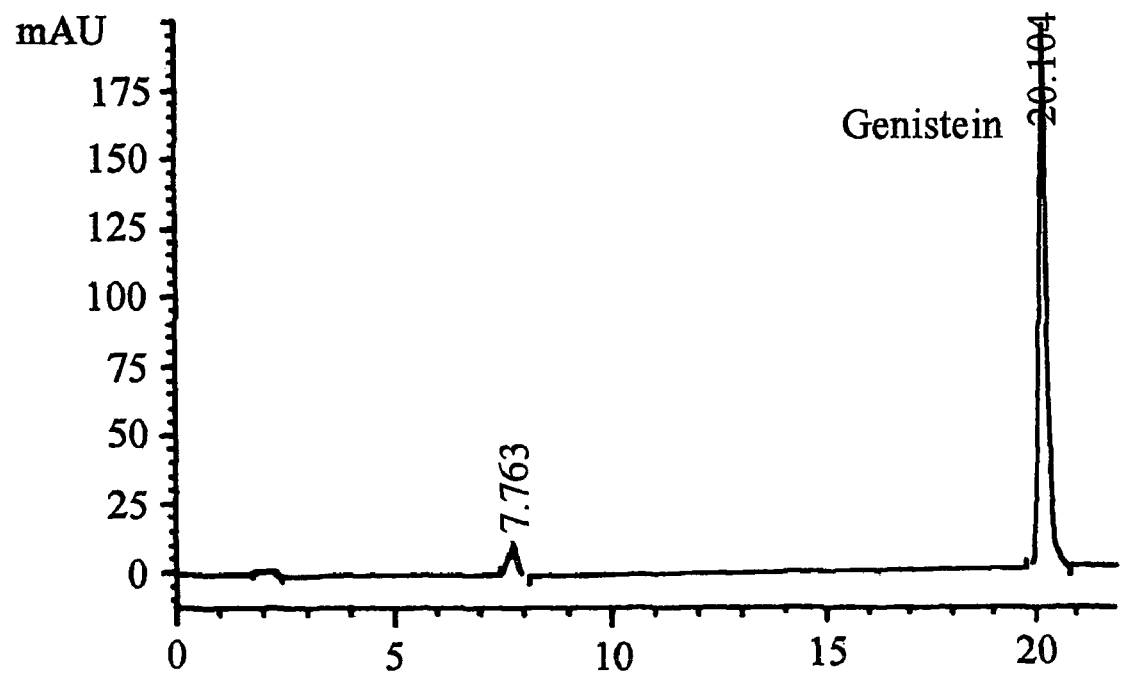
FIG. 1A is a chromatogram showing the isoflavone content of a *Sophorae Fructus* extract prepared by the method of the invention, which was analyzed by HPLC.

To accomplish the object of the invention, the present invention provides a method for preparing a *Sophorae Fructus* extract containing a high concentration of isoflavone.

In particular, the present invention provides a method for preparing a *Sophorae Fructus* extract containing a high concentration of isoflavone, which comprises the following steps:

(a) hydrothermally extracting *Sophorae Fructus* by adding water to the *Sophorae Fructus* and heating;

(b) removing a precipitate by cooling and filtering the extract to produce a filtrate;

(c) treating the filtrate with amylase or pectinase;

(d) recovering a precipitate by centrifuging the enzyme treated solution and adding ethanol to the precipitate; and (e) recovering a supernatant by centrifuging the ethanol added solution.

"*Sohporae Fructus*" used herein refers to a fruit of *Sophora japonica Linne*, a deciduous arbor belonging to a pea family (Leguminosae). Preferably, *Sohporae Fructus* means a mature fruit of *Sophora japonica Linne*. It is preferable that *Sophorae Fructus* of the present invention is a mature fruit of *Sohpora japonica Linne* having its unique color and flavor without other taste and smell. It is also preferable that the peel of the fruit is khaki brown or brown and the seed is black or black brown.

In the course of conducting studies to find out a natural source of isoflavone other than a soy bean, the present inventors identified that *Sophorae Fructus* itself contains about 29.58 g/kg of isoflavone in high concentration in the form of aglycone (see Experimental Example 1). It has been reported that a soy bean generally contains about 0.5~1.7 g/kg of isoflavone in the form of aglycone depending on a kind (So E. H. et al., *Korean J. Breed.*, 33(1), 35~39, 2001).

Accordingly, the present invention provides a method for preparing a *Sophorae Fructus* extract containing a high concentration of isoflavone using *Sophorae Fructus* as a new source of isoflavone under the optimum conditions as explained below.

The present invention will be described in detail.

The method for preparing a *Sophorae Fructus* extract of the present invention will be described hereinafter step by step.

Step 1: Hydrothermal Extraction

Water is added to *Sophorae Fructus*, followed by heating for hydrothermal extraction. At this time, *Sophorae Fructus* can be used right after being harvested and washed or after being additionally dried. Methods for dry *Sophorae Fructus* comprise sun drying, shade drying, hot air drying, natural drying and the like. In addition, *Sophorae Fructus* or its dried body can be crushed into powder to enhance the efficiency of the extraction. The dried *Sophorae Fructus* can be crushed preferably in 10~100 mesh size, more preferably in 20~40 mesh size.

There is no fixed ratio of *Sophorae Fructus* to water for hydrothermal extraction, but usually 3~20 (based on weight) is preferable and 5~10 (based on weight) is more preferable.

The proper temperature for hydrothermal extraction, rages from 100 to 130° C., and 120~125° C. is preferred. The pressure for hydrothermal extraction is adjusted to 1.0~2.0 kgf/cm$^2$, and preferably to 1.5~1.6 kgf/cm$^2$.

The extraction time depends on the extraction temperature, but 1~6 hours are general and 1-3 hours are preferred. In addition, if a shaker is used in extraction, the efficiency of the extraction is more enhanced.

Step 2: Filtration of Hydrothermal Extract and Elimination of Precipitate

The hydrothermal extract prepared in the above step 1 is cooled enough to prevent a precipitate from floating, and then filtered to remove the precipitate. At this time, the hydrothermal extract is cooled to 40~60° C., and preferably 50~55° C. The filtration of the hydrothermal extract is performed by known methods. The methods of filtration comprise, for example, centrifugation, membrane filter and filter cloth, and filter cloth is preferable in the invention. Most preferably, the cooled hydrothermal extract is filtered with 100 mesh filter cloth, and then, filtered again with 200 mesh filter cloth to completely remove insoluble precipitate.

Step 3: Enzyme Treatment

In general, isoflavone is contained in plants in the form of glycoside-type, that is, isoflavone compound is combined with sugar therein. However, in this invention, in order to obtain isoflavone from *Sophorae Fructus* in the form of aglycon-type having excellent bio-absorbability, in which isoflavone is not combined with sugar, the filtrate of the step 2 is treated with an enzyme, so that gylcoside-type isoflavone can be hydrolyzed into aglycon-type isoflavone. At this time, α-amylase, β-amylase or pectinase can be used as the enzyme.

For enzyme treatment, the filtrate is heated to the temperature which is proper for enzyme reaction. The temperature of the filtrate is adjusted to 40~60° C. and preferably 52±3° C. The heated filtrate is treated with an enzyme by 0.01~1% (v/v) and preferably 0.1~0.5% (v/v). The filtrate treated with an enzyme is shaken for 4~24 hours and preferably 12~16 hours, leading to hydrolysis.

Step 4: Centrifugation of Enzyme Treated Solution and Ethanol Extraction

The enzyme treated solution of the above step 3 is immediately centrifuged to recover a precipitate. Ethanol is added to the recovered precipitate in order to extract isoflavone. Unlike sugar or protein, aglycon-type isoflavone is dissolved in ethanol. So, purer isoflavone can be obtained by extracting the precipitate recovered by enzyme treatment using ethanol. At this time, 100% ethanol is diluted with water, resulting in 80~100% ethanol and preferably 90~95% ethanol. The diluted ethanol is added to the precipitate in the ratio of 5~10 to 1. Then, the enzyme treated solution is shaken for 30~60 minutes until the precipitate is completely dispersed, and left for 60~120 minutes.

Step 5: Centrifugation of Ethanol Added Solution and Recovery of Supernatant

The ethanol added solution of the above step 4 is centrifuged to remove a precipitate, and then, supernatant containing isoflavone in high concentration is recovered.

The recovered supernatant can be concentrated, followed by spray drying to powder it. The concentration can be performed by heating the supernatant with a batch or continuous concentrator. Ethanol evaporated during the concentration is cooled and then recovered for recycling. The concentrated solution in which ethanol was eliminated is powdered by spray drying using a spray drier.

When *Sophorae Fructus* extract is prepared by said method of the present invention, extract containing a high concentration of isoflavone can be obtained.

In the case of the methanol extract of a soybean, genistein contained in the extract is 0.1~2.4 g/kg and isoflavone therein is 11~12 g/kg (Korean patent publication No. 2001-47621). Also, in the case of the extract of non-oil soybean powder or a mature soybean, isoflavone in the extract is 15~43% (150~430 g/kg) (Korean patent No. 388511).

On the contrary, when the extract of *Sophorae Fructus* is prepared by the method of the present invention, isoflavone contained in the extract is 876.6 g/kg.

Thus, the method of the present invention can obtain a *Sophorae Fructus* extract containing a higher concentration of isoflavone than the conventional method by preparing a *Sophorae Fructus* extract under the optimum conditions using *Sohporae Fructus* as a new source of isofalvone.

EXAMPLES

Practical and presently preferred embodiments of the present invention are illustrated as shown in the following Examples.

However, it will be appreciated that those skilled in the art, on consideration of this disclosure, may make modifications and improvements within the spirit and scope of the present invention.

Example 1

Preparation of *Sophorae Fructus* Extract According to the Present Invention 10 g of *Sophorae Fructus* (Jesung Pharmaceutical Co., Kyungdong Market, Korea) was crushed into 30-mesh size by using a dry-pulverizer. Drinking water was added to the above crushed *Sohporae Fructus* to dilute by 10 times (pulverized material:drinking water=9:1), and the solution was heated at 121° C. for 2 hours under the pressure of 1.5 kgf/cm$^2$. Then, the solution was cooled to 50° C., followed by filtering with a 100 mesh filter cloth and second filtering with a 200-mesh filter cloth to remove precipitate and obtain filtrate. Amylase (Pectinase 100 L, Novo Co.). was added to the above filtrate by the concentration of 0.5% (v/v), and enzyme reaction was performed at 50° C. for 16 hours. The reaction solution was centrifuged to recover precipitate, and 90% ethanol was added to the recovered precipitate 5 times as much as the precipitate. The ethanol mixture was shaken for 30 minutes until the precipitate was completely dispersed. After shaking, the solution was left for 1 hour, and then, centrifuged to remove precipitate and recover supernatant. The supernatant was concentrated to the volume of one tenth using a concentrator, and the concentrate was powdered using a spray dryer to obtain 0.3 g of *Sophorae Fructus* extract powder (yield to crushed material of *Sophorae Fructus*: 3%).

Example 2

Analysis of Isoflavone Contained in *Sohporae Fructus* Extract Prepared by the Method of the Present Invention Isoflavone content contained in a *Sophorae Fructus* extract prepared in Example 1 was analyzed by using high performance liquid chromatography (HPLC).

1 mg of the *Sophorae Fructus* extract powder prepared in Example 1 was taken and dissolved completely in 1 ml of 100% methanol, resulting in 100-fold dilution. The solution was filtered by using a syringe filter (0.45 μm, Waters Korea). 10 μl of filtrate was taken and used as a sample for HPLC analysis. C18 ODS (150×4.6 mm, S-4 μm, 80 A) (YMC Co., Japan) was used as a column for HPLC. The analysis was started with a mixed solvent as mobile phase in which 1% acetic acid was added and acetonitrile was mixed with water in the volume ratio of 20:80, and in 30 minutes, gradient was performed with another mixed solvent in which 1% acetic acid was added and acetonitrile was mixed with water in the volume ratio of 40:60. The analysis was performed at room temperature at 0.8 ml/min of flow speed, and $OD_{280}$ was measured.

Aglycon-type daidzein (Sigma, USA), glycitein (Sigma, USA) and genistein (Sigma, USA) were used as standard materials for the quantification.

Figure 1B:
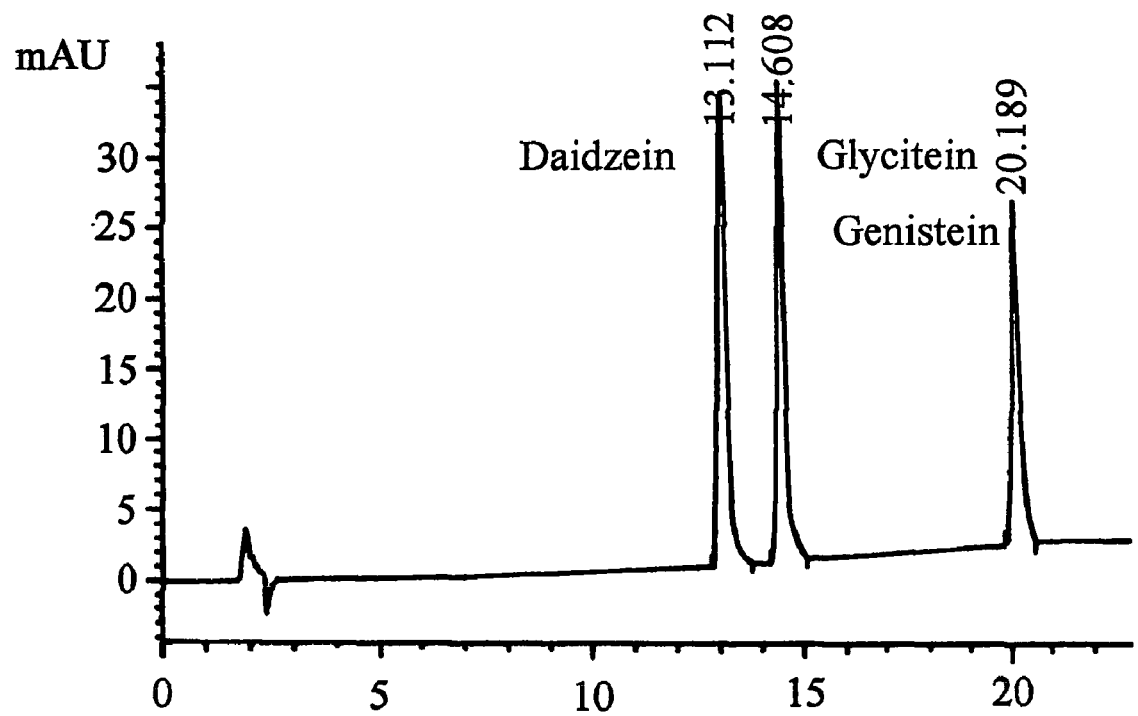
FIG. 1B is a chromatogram of standard materials used for HPLC analysis of the isoflavone content of a *Sophorae Fructus* extract prepared by the method of the invention.

As a result, isoflavone content in the *Sophorae Fructus* extract prepared in Example 1 was 876.6 g/kg (87.6%) (FIGS. 1A and 1B).

Therefore, it was confirmed that the *Sophorae Fructus* extract prepared by the method of the present invention contained isoflavone in a very high concentration.

Experimental Example 1

Analysis of Isoflavone Content in *Sophorae Fructus* Itself

The content of isoflavone contained in *Sophorae Fructus* was analyzed. Hydrothermal extract of *Sophorae Fructus* was prepared by using the same method as Example 1. 5 ml of 4N HCl was mixed with 5 ml of the hydrothermal extract of *Sophorae Fructus*. Reflux cooling was performed in a 100° C. water bath for 2 hours, leading to acid hydrolysis. The solution recovered after acid hydrolysis was put in a flask and methanol was added thereto to make the total volume 50 ml (10-fold dilution). Then, 10 ml of the solution was taken and diluted with methanol to make total volume 100 ml (10-fold dilution). After pH was adjusted to 4~8, the solution was filtrated through a filter. HPLC analysis was performed using the filtrate as a sample by the same method as Example 2, thereby aglycon-type isoflavone content in *Sophorae Fructus* was measured.

As a result, isoflavone content in *Sophorae Fructus* itself was 29.58 g/kg (2.96%). From this result, it was confirmed that a high concentration of isoflavone was contained in *Sophorae Fructus*.

Experimental Example 2

Comparison of Isoflavone Concentrations in *Sophorae Fructus* Extracts According to Extraction Methods In order to establish a suitable extraction method for preparing a *Sophorae Fructus* extract containing a high concentration of isoflavone, isoflavone contents in *Sophorae Fructus* extracts according to various extraction methods were compared. The extraction methods were exemplified by an extraction method using hexane and 60% ethanol solvent, an extraction method using hexane and water in order, an extraction method using only ethanol solvent, and an extraction method using just water.

<2-1> Preparation of a *Sophorae Fructus* Extract by the Method Using Hexane and 60% Ethanol 100 ml of hexane was added to 10 g of crushed *Sophora Fructus* prepared in Example 1, and extraction was performed for 2 hours to remove lipid. The extract was centrifuged to recover precipitate. 100 ml of 60% ethanol was added to the precipitate, followed by sonication for 30 minutes. The extract was, then, filtrated to recover supernatant, followed by freeze-drying. As a result, 2.4 g of *Sophorae Fructus* extract was obtained.

<2-2> Preparation of *Sophorae Fructus* Extract by the Method Using Hexane and Water 100 ml of hexane was added to 10 g of crushed *Sophorae Fructus* prepared in Example 1, and extraction was performed for 2 hours to remove lipid. The extract was centrifuged to recover precipitate. Drinking water was added to the extract by 10-fold large volume, which was heated at 100° C. for 6 hours for hydrothermal extraction. The hydrothermal extract was filtered and supernatant was recovered. The recovered supernatant was freeze-dried to obtain 2.8 g of *Sophorae Fructus* extract.

<2-3> Preparation of *Sophorae Fructus* Extract by the Method Using 60% Ethanol 100 ml of 60% ethanol was added to 10 g of crushed *Sophorae Fructus* prepared in Example 1, and sonication was performed for 30 minutes. The extract was filtered and supernatant was recovered. The recovered supernatant was freeze-dried to obtain 2.5 g of *Sophorae Fructus* extract.

<2-4> Preparation of *Sophorae Fructus* Extract by the Method Using Water 10 g of crushed *Sophorae Fructus* obtained in Example 1 was diluted by ten times with drinking water (crushed *Sophorae Fructus*:drinking water=9:1). And hydrothermal extraction was performed by heating at 100° C. for 6 hours. The extract was filtrated to remove precipitate and obtain supernatant, 2.6 g of *Sophorae Fructus* extract.

<2-5> Analysis of Isoflavone Contents in *Sophorae Fructus* Extracts According to Extraction Methods Isoflavone contents in *Sophorae Fructus* extracts prepared in Experimental Examples <2-1> through <2-4> were analyzed by high performance liquid chromatography (HPLC).

Each *Sophorae Fructus* extract prepared in the above Experimental Examples was hydrolyzed with acid by the same method as Experimental Example 1 and analyzed by HPLC by the same method as Example 2.

As a result, in the case of Experimental Example <2-1> using hexane and 60% ethanol as an extraction solvent, total isoflavone content was 2.13% (21.3 g/kg), and in the case of Experimental Example <2-2> using hexane and water, total isoflavone content was 2.64% (26.4 g/kg). In the case of Experimental Example <2-3> using 60% ethanol as an extraction solvent, total isoflavone content was 3.42% (34.2 g/kg), and in the case of Experimental Example <2-4> performed with hydrothermal extraction using only water, total isoflavone content was 3.38% (33.8 g/kg) (Table 1). Therefore, it could be known that the extract prepared by the method using ethanol have the highest isoflavone content of all. Extract prepared by hydrothermal extraction had the second highest isoflavone content, which was not much different from the content in the extract prepared by using ethanol.

Meanwhile, there is a disadvantage that ethanol ought to be removed completely before enzyme treatment, in order to perform enzyme treatment step converting to aglycon-type isoflavone after ethanol extraction of *Sophorae Fructus*. Thus, it was proved that the hydrothermal extraction is the best method for the preparation of the *Sophorae Fructus* extract.

TABLE 1

Isoflavone contents in *Sophorae Fructus* extracts according to extraction methods

| Extraction method | Isoflavone content (%) | | | Concentration of total isoflavone (%) |
|---|---|---|---|---|
| | Daidzein | Glycitein | Genistein | |
| Hexane/60% ethanol | 0.02 | 0.03 | 2.08 | 2.13 |
| Hexane/water | 0.03 | 0.00 | 2.61 | 2.64 |
| 60% ethanol | 0.00 | 0.01 | 3.41 | 3.42 |
| Water | 0.00 | 0.00 | 3.38 | 3.38 |

Experimental Example 3

Comparison of Isoflavone Content in *Sophorae Fructus* Extracts According to Temperature and Time of Hydrothermal Extraction Each *Sophorae Fructus* extract was prepared by the same method as Example 1 except varied extraction temperature and time. Each *Sophorae Fructus* extract prepared above was hydrolyzed with acid by the same method as Experimental Example 1 and analyzed by HPLC by the same method as Example 2.

As a result, when a extraction temperature was over 100° C., isoflavone content was high, suggesting that the range of preferable extraction temperature is 100° C.~130° C. (Table 2).

TABLE 2

Concentration of total isoflavone in *Sophorae Fructus* extracts according to extraction temperature

| Extraction temperature (° C.) | Concentration of total isoflavone (%) |
|---|---|
| 80 | 2.8% |
| 90 | 3.2% |
| 100 | 3.39% |
| 110 | 3.41% |
| 120 | 3.52% |
| 130 | 3.42% |

In addition, when extraction lasted for more than 2 hours, isoflavone content was high, suggesting that the preferable extraction time is 2~3 hours.

TABLE 3

Concentration of total isoflavone in *Sophorae Fructus* extracts according to extraction time

| Extraction time | Concentration of total isoflavone (%) |
|---|---|
| 1 h | 2.94 |
| 2 h | 3.42 |
| 3 h | 3.46 |
| 4 h | 3.39 |

Experimental Example 4

Comparison of Conversion Into Aglycon-Type Isoflavone in *Sophorae Fructus* Extracts According to Enzyme Treatment We investigated the levels of conversion of glycoside-type isoflavone into aglycon-type isoflavone in *Sophorae Fructus* extracts according to whether enzyme was treated or not. It has generally been known that acid hydrolysis is effective for the conversion of glycoside-type isoflavone to aglycon-type isoflavone, but the method does harm when it is applied to the production of food. So, enzyme treatment method was used instead in the present invention. The efficiency of the conversion of glycoside-type isoflavone into aglycon-type isoflavone by enzyme treatment method was compared with that by acid hydrolysis method.

A *Sophorae Fructus* extract not treated with an enzyme was prepared by hydrothermal extraction and filtration using the same method as Example 1, but the obtained filtrate was not treated with an enzyme. On the other hand, a *Sophorae Fructus* extract treated with an enzyme was prepared by preparing hydrothermal extract and treating the extract with amylase using the same method as Example 1. The isoflavone contents of the extracts prepared above were measured by the same method as Example 2. The conversion rates of isoflavone into aglycon-type according to the enzyme treatment were calculated considering the isoflavone content in the *Sophorae Fructus* extract measured by HPLC analysis after acid hydrolysis in Experimental Example 1, as 100%.

As a result, the conversion rate of gylcoside-type isoflavone to aglycon-type isoflavone of *Sophorae Fructus* extract treated with an enzyme was 97%, which was not much different from that of *Sophorae Fructus* extract hydrolyzed with acid, but much higher than that of *Sophorae Fructus* extract not treated with an enzyme (Table 4).

TABLE 4

Comparison of conversion rates of glycoside-type isoflavone into aglycon-type isoflavone in *Sophorae Fructus* extracts according to enzyme treatment

| | Acid hydrolysis | Enzyme treatment | Without enzyme treatment |
|---|---|---|---|
| Aglycon-type isoflavone content (%) | 100% | 97% | 5% |

Experimental Example 5

Comparison of Isoflavone Contents in *Sophorae Fructus* Extracts According to Ethanol Extraction We investigate the effect of ethanol treatment on *Sophorae Fructus* extracts prepared by hydrothermal extraction and subsequent enzyme treatment using the same method as Example 1 on isoflavone content thereof.

For this purpose, using the same method as Example 1, hydrothermal extraction, enzyme treatment and ethanol extraction were performed with *Sophorae Fructus* to recover supernatant. Then, the recovered supernatant was concentrated and powdered using a spray dryer to obtain 0.3 g of powder extract of *Sophorae Fructus*.

In addition, using the same method as Example 1 except ethanol extraction, hydrothermal extraction and enzyme treatment were performed with *Sophorae Fructus* to recover extract. Then, the recovered extract was concentrated and powdered using a spray dryer to obtain 2.4 g of powder extract of *Sophorae Fructus*.

The isoflavone content of each *Sophorae Fructus* extract prepared above was analyzed by the same method as Example 2.

As a result, it was confirmed that the isoflavone content of *Sophorae Fructus* extract with ethanol extraction was higher than that of another extract without ethanol extraction (Table 5).

TABLE 5

Isoflavone contents in *Sophorae Fructus* extracts according to ethanol extraction

| | Ethanol extraction | Non-ethanol extraction |
|---|---|---|
| Isoflavone content (%) | 87.64% | 16.67% |

The entire disclosure of Korean Patent Application No. 2003-77000, filed on Oct. 31, 2003 including its specification, claims, drawings and summary are incorporated herein by reference in its entirety.

INDUSTRIAL APPLICABILITY

As explained above, a *Sophorae Fructus* extract containing a high concentration of aglycon-type isoflavone having an excellent bio-absorbability can be prepared by the method of the present invention.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for preparing an extract of a fruit of *Sophora japonica* containing isoflavone comprising the following steps: (a) hydrothermally extracting the fruit of *Sophora japonica* by adding water to the fruit of *Sophora japonica* and heating; (b) removing a precipitate by cooling and filtering the extract to produce a filtrate; (c) treating the filtrate with amylase or pectinase; (d) recovering a precipitate by centrifuging the enzyme treated solution and adding ethanol to the precipitate; and (e) recovering a supernatant by centrifuging the ethanol added solution.

2. The method of claim 1, wherein the fruit of *Sophora japonica* of step (a) is used after pulverization.

3. The method of claim 1, wherein the hydrothermally extracting of step (a) is performed at 100-130° C. for 1-6 hours after adding 3-20 parts water per 1 part fruit of *Sophora japonica* (w/w) to the fruit of *Sophora japonica*.

4. The method of claim 1, wherein the extract of step (b) is cooled to 40-60° C.

5. The method of claim 1, wherein step (c) is performed by heating the filtrate to 40-60° C., adding amylase or pectinase to 0.01-1% (v/v) to the filtrate, and reacting the filtrate for 4-24 hours.

6. The method of claim 1, wherein the precipitate of step (d) is shaken for 30-60 minutes after adding 5-10 parts ethanol per 1 part precipitate (w/w) to the precipitate, and left for 60-120 minutes.

7. The method of claim 1, wherein the method comprises an additional step of concentrating the supernatant of step (e).

8. The method of claim 7, wherein the method comprises an additional step of pulverizing the concentrate by spray drying.

* * * * *